(12) United States Patent
Park

(10) Patent No.: US 9,949,484 B2
(45) Date of Patent: Apr. 24, 2018

(54) ANTIMICROBIAL POLYURETHANE MATERIALS AND METHODS OF FORMING AND USING SAME

(71) Applicant: The Regents of the University of Colorado, a body corporate, Denver, CO (US)

(72) Inventor: Daewon Park, Greenwood Village, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 63 days.

(21) Appl. No.: 14/398,393

(22) PCT Filed: May 1, 2013

(86) PCT No.: PCT/US2013/039136
§ 371 (c)(1),
(2) Date: Oct. 31, 2014

(87) PCT Pub. No.: WO2013/166198
PCT Pub. Date: Nov. 7, 2013

(65) Prior Publication Data
US 2015/0132248 A1    May 14, 2015

Related U.S. Application Data

(60) Provisional application No. 61/641,172, filed on May 1, 2013.

(51) Int. Cl.
| | |
|---|---|
| *A01N 47/20* | (2006.01) |
| *C08G 18/83* | (2006.01) |
| *A61L 27/18* | (2006.01) |
| *A61L 31/06* | (2006.01) |
| *A61L 31/16* | (2006.01) |
| *D03D 15/00* | (2006.01) |
| *A61L 2/232* | (2006.01) |

(52) U.S. Cl.
CPC .......... *A01N 47/20* (2013.01); *A61L 27/18* (2013.01); *A61L 31/06* (2013.01); *A61L 31/16* (2013.01); *C08G 18/833* (2013.01); *D03D 15/00* (2013.01); *A61L 2/232* (2013.01); *A61L 2300/208* (2013.01); *A61L 2300/404* (2013.01); *A61L 2400/12* (2013.01); *C08G 2340/00* (2013.01); *Y10T 428/2982* (2015.01)

(58) Field of Classification Search
None
See application file for complete search history.

(56) References Cited

U.S. PATENT DOCUMENTS

| | | | | |
|---|---|---|---|---|
| 4,046,725 A | * | 9/1977 | Pusineri | A61L 33/0023 523/112 |
| 5,371,166 A | * | 12/1994 | Farkas | C08G 18/0814 523/181 |
| 2008/0107707 A1 | * | 5/2008 | Lawson | A61K 31/397 424/423 |
| 2008/0213394 A1 | * | 9/2008 | Tullo | A01N 59/16 424/618 |
| 2010/0204515 A1 | * | 8/2010 | Chasser | C08G 18/025 564/252 |

FOREIGN PATENT DOCUMENTS

| | | | |
|---|---|---|---|
| JP | 1238565 | * | 9/1989 |
| WO | WO2009148880 | * | 12/2009 |

OTHER PUBLICATIONS

Pub Chem, 4,4'-Diphenylmethane diisocyanate, http://pubchem.ncbi.nlm.nih.gov/compound/4_4_-Diphenylmethane_diisocyanate, retrieved online on Sep. 29, 2015.*
Chen, Functional Nanostructured Materials: Synthetic Aspects & Properties Evaluation, Aug. 10, 2011, p. 1-141.*
Wikipedia—polyurethane, https://wikipedia.org/wiki/Polyurethane, retrieved online Oct. 27, 2015.*
Park, A functionalizable reverse thermal gel based on a polyurethane/PEG block copolymer, Biomaterials 32 (2011) 777-786.*
Grapski et al., Synthesis and characterization of non-leaching biocidal polyurethanes, Biomaterials 22 (2001) 2239-2246.*
Subbiah, T. et al., Electrospinning of Nanofibers, Journal of Applied Polymer Science, 2005, pp. 557-569, vol. 96, Wiley Periodicals, Inc.
Haldar, J. et al., Polymeric Coatings that Inactivate Both Influenza Virus and Pathogenic Bacteria, Applied Biological Sciences, Nov. 21, 2006, pp. 17667-17671, vol. 103, PNAS.
Xie, Y. et al., Synthesis and Characterization of Water-Soluble Chitosan Derivate and its Antibacterial Activity, Carbohydrate Polymers, 2007, pp. 142-147, vol. 69, Elsevier Ltd.
Murata, H. et al., Permanent, Non-Leaching Antibacterial Surfaces—2: How High Density Cationic Surfaces Kill Bacterial Cells, Biomaterials, 2007, pp. 4870-4879, vol. 28, Elsevier Ltd.

(Continued)

*Primary Examiner* — Jennifer A Berrios
(74) *Attorney, Agent, or Firm* — Snell & Wilmer L.L.P.

(57) ABSTRACT

Antimicrobial quaternized polyurethane materials and methods of forming and using the materials are disclosed. The quaternized polyurethane antimicrobial materials may be synthesized from one or more diisocyanates and one or more diols or triols. The quaternized polyurethane materials may be stand alone or coated onto other surfaces, such as medical devices, table tops, air/water filters, or the like to provided desired antimicrobial devices and surfaces.

32 Claims, 9 Drawing Sheets

(56) References Cited

OTHER PUBLICATIONS

Hsu, B. et al., Mechanism of Inactivation of Influenza Viruses by Immobilized Hydrophobic Polycations, Applied Biological Sciences, Jan. 4, 2011, pp. 61-66, vol. 108, PNAS.
Larson, A. et al., Hydrophobic Polycationic Coatings Disinfect Poliovirus and Rotavirus Solutions, Biotechnology and Bioengineering, Mar. 1, 2011, pp. 720-723.

* cited by examiner

ANTIMICROBIAL POLYURETHANE MATERIALS AND METHODS OF FORMING AND USING SAME

CROSS REFERENCE TO RELATED APPLICATIONS

This application is the national stage entry of International Application No. PCT/US2013/039136, entitled ANTIMICROBIAL POLYURETHANE MATERIAL AND METHOD OF FORMING AND USING SAME, filed on May 1, 2013, and claims the benefit of U.S. Provisional Patent Application Ser. No. 61/641,172, entitled ANTIMICROBIAL POLYURETHANE MATERIAL AND METHOD OF FORMING AND USING SAME, and filed May 1, 2012, the disclosures of which are incorporated herein by reference to the extent such disclosures do not conflict with the present disclosure.

FIELD OF INVENTION

The present invention generally relates to antimicrobial materials. More particularly, the invention relates to polyurethane materials having antibacterial and antiviral (or bactericidal and virucidal) properties.

BACKGROUND OF THE INVENTION

Infections and infectious diseases can be caused by a variety of pathogens, including viruses, bacteria, fungi, and the like. Unfortunately, a variety of surfaces, such as ventilation ducts, household, hospital, office furniture, fabrics, toys, and other surfaces, as well as contaminated water supplies, onto or into which the pathogens are transmitted, can serve as reservoirs and breeding grounds for such pathogens.

Various materials have been developed to mitigate the spread of such pathogens. For example, immobilized hydrophobic polymerized quaternary ammonium compounds (polyQACs), based on polyethylenimine (PEI), which exert antimicrobial action by disrupting cell walls and/or outer membranes of bacteria and fungi have been developed. In addition, polyQACs, such as N,N-dodecyl, methyl-PEI have recently been reported to inactivate envelope viruses, including both human and avian strains of influenza viruses, and to disinfect solutions containing non-enveloped polio virus and rotavirus.

While such polyQAC materials may work for some applications, the polyQAC materials may exhibit relatively poor impact strength, abrasion resistance, and may lack desired versatility (e.g., ability to alter material properties during the polymerization process and ability to alter material morphology). Accordingly, improved antimicrobial compounds that are relatively easy to form and that exhibit improved impact strength, abrasion resistance, and versatility are desired.

SUMMARY OF THE INVENTION

The present invention generally relates antimicrobial materials based on polyurethane (PU). Antimicrobial materials based on polyurethane may have several advantages over other antimicrobial materials, because polyurethane is ubiquitous, versatile, and exhibits excellent impact strength and abrasion-resistance characteristics, relative to other polymer-based antimicrobial materials. The polyurethane antimicrobial materials may be stand alone or coated onto other surfaces, such as surface of medical devices, table tops, air or water filters, or the like to provide antimicrobial surfaces on such devices.

In accordance with exemplary embodiments of the invention, an antimicrobial composition comprises quaternized polyurethane. In accordance with various aspects of these embodiments, a mer of a quaternized polyurethane comprises a quaternary compound. In accordance with further aspects, the an end or terminal group of the quaternized polyurethane comprises a quaternary compound. In accordance with yet additional aspects of these embodiments, a quaternary group comprises

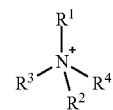

where $R^1$ comprises a polyurethane backboned and $R^2$-$R^4$ comprise a group selected from $[H(H_2C)_n]_m$ and $(CH_3)_{3-m}$, where m is 2 or 3 and n may range from, for example 6-22.

In accordance with yet further exemplary aspects of these embodiments, quaternized polyurethane may include from about 25 to 140 repeating quaternized polyurethane mers and the molecular weight of the polymer may range from about 5000 to about 50,000 Da or about 10,000 to about 30,000 Da.

In accordance with yet additional aspects of these embodiments, the antimicrobial polyurethane is synthesized from one or more diisocyanates and one or more compounds selected from the group of one or more diols comprising an amine group and one or more triols comprising an amine group. The amine groups may initially be protected by protecting groups, such as BOC groups, which are later removed as the quaternary groups are formed. Exemplary diisocyanate groups include isophorone diisocyanate, 1,4-phenylene diisocyanate, 1,3-phenylene diisocyanate, toluene-2,4-diisocyanate, toluene-2,6-diisocyanate, 2,4,6-trimethyl-1,3-phenylene diisocyanate, tetramethylene diisocyanate, octamethylene diisocyanate, 1,3-bis(1-isocyanato-1-methylethyl)benzene, 4,4'-methylenebis(phenyl isocyanate), 3,3'-dimethyloxy-4,4'-bisphenylene diisocyanate, 1,8 diisocyanateoctane, α,α,α',α'-tetramethyl-1,3-xylylene diisocyanate, and 3,3'-dimethoxy-4,4'-biphenylene diisocyanate. Exemplary diol compounds include serinol, 3-dimethylaminopropane-1,2-diol, 2-amino-2-methyl-1,3-propanediol, 2-amino-1,1-propanediol, 2-aminobutane-1,4-diol, 2-amino-1,2-propanediol, 2-amino-1,6-hexanediol, 2,5-diamino-1,6-hexanediol, 2-amino-1,7-heptanediol, 2-amino-1,5-pentanediol, 2-amino-2-ethyl-1,3-propanediol, 2,3-diamino-1,4-butanediol, 2,4-diamino-1,5-pentanediol, 2-amino-1,3-octanediol, 4-amino-3,5-heptanediol, 4-amino-1,3-hexanediol, 2-amino-2-isopropyl-1,3-propanediol, 4-amino-1,3-heptanediol, 2-amino-1,2,4-trideoxypentitol, 2,4-diamino-1,6-hexanediol. Exemplary triol compounds include any triols including three hydroxyl groups and one amine group, such as triethanolamine.

In accordance with various embodiments of the invention, the quaternized polyurethane material is in the form of nanoparticles (e.g., having an average diameter of about 25 nm to 300 nm or about 100 nm to about 300 nm). In accordance with additional embodiments, the quaternized polyurethane material is in the form of nanofibers (e.g., having an average diameter of about 150 nm to about 300 nm). In accordance with further embodiments, the quaternized polyurethane material is in a suspension (e.g., aqueous). Alternatively, the quaternized polyurethane material is in a solution (e.g., organic).

In accordance with further embodiments, a device (e.g., a filter, table, medical device, or the like) includes a surface and a quaternized polyurethane as described herein coated onto the surface.

In accordance with yet further embodiments, a method of forming a quaternized polyurethane material includes the steps of dissolving a one or more diols or triols, the diols or triols having an amine group protected with a protecting group (e.g., N-BOC-serinol), in a solvent (e.g., DMF) to form a solution, adding one or more diisocyanates (e.g., MDI) to the solution, polymerizing the solution to form polyurethane (e.g., under an nitrogen environment), precipitating the polyurethane, optionally purifying the polyurethane, removing the protecting groups, and forming the quaternized polyurethane. In accordance with various aspects of these embodiments, the polymerizing step is performed in a nitrogen environment. In accordance with further aspects, the method further includes a step of forming nanoparticles including the quaternized polyurethane. In accordance with yet additional aspects, the method includes the step of forming nanofibers including the quaternized polyurethane.

BRIEF DESCRIPTION OF THE DRAWING FIGURES

A more complete understanding of exemplary embodiments of the present disclosure may be derived by referring to the detailed description and claims when considered in connection with the following illustrative figures.

Figure 1:
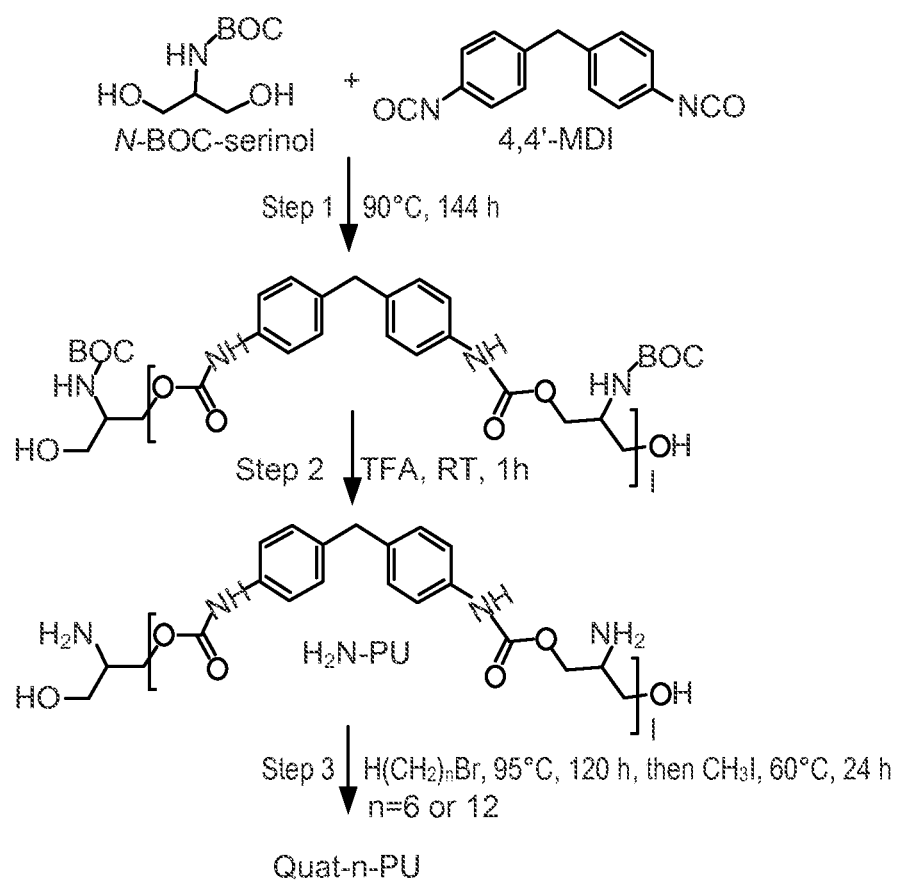
FIG. 1 illustrates a method of forming quaternized polyurethane in accordance with exemplary embodiments of the disclosure.

It will be appreciated that the figures are not necessarily drawn to scale. For example, the dimensions of some of the elements in the figures may be exaggerated relative to other elements to help to improve understanding of illustrated embodiments of the present invention.

DETAILED DESCRIPTION OF PREFERRED EMBODIMENTS OF THE INVENTION

The description of exemplary embodiments of the present invention provided below is merely exemplary and is intended for purposes of illustration only; the following description is not intended to limit the scope of the invention disclosed herein. Moreover, recitation of multiple embodiments having stated features is not intended to exclude other embodiments having additional features or other embodiments incorporating different combinations of the stated features.

The present disclosure provides an antimicrobial polyurethane material and methods of forming and using the material. As set forth in more detail below, the polyurethane material includes quaternized groups or moieties on a polyurethane backbone to provide antimicrobial material having desirable characteristics.

In accordance with exemplary embodiments of the disclosure, a quaternized polyurethane compound includes a general formula of

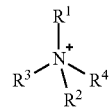

where $R^1$ comprises a polyurethane backboned and $R^2$-$R^4$ comprise a group selected from $[H(H_2C)_n]_m$ and $(CH_3)_{3-m}$, where m is 2 or 3. Quaternized polyurethane polymers in accordance with various embodiments of the disclosure can be designated as Quat-n-PU, where n corresponds to a number of methylene groups, $(H_2C)_n$, in the quaternizing compound. Exemplary values for n range from 6 to 22, 6 to 12, or may be 6, 8, 12, 14, 18, or 22.

The polyurethane backbone may be formed in a variety of ways. For example, an amine-bearing polyurethane backbone may be synthesized from a suitable diol or triol (e.g., amine bearing diols or triols) and a diiocyanate compound. A number of repeating mers, 1, in the quaternized polyurethane may depend on the synthesizing process and/or the diol and/or triol used to synthesize the quaternized polyurethane material. By way of examples, a quaternized polyurethane polymer includes from about 20 to 200 or from about 25 to about 140 mers. Exemplary molecular weights of the antimicrobial quaternized polyurethanes range from about 5,000 to about 50,000 or 10,000 to about 30,000 Da. The ends of the polymer may include hydroxyl and/or quaternized amine functional groups.

Exemplary diisocyanates suitable for use in synthesizing quaternized polyurethanes in accordance with the present invention include, but are not limited to isophorone diisocyanate, 1,4-phenylene diisocyanate, 1,3-phenylene diisocyanate, toluene-2,4-diisocyanate, toluene-2,6-diisocyanate, 2,4,6-trimethyl-1,3-phenylene diisocyanate, tetramethylene diisocyanate, octamethylene diisocyanate, 1,3-bis(1-isocyanato-1-methylethyl)benzene, 4,4'-methylenebis(phenyl isocyanate), 3,3'-dimethyloxy-4,4'-bisphenylene diisocyanate, 1,8 diisocyanateoctane, α,α,α',α'-tetramethyl-1,3-xylylene diisocyanate, and 3,3'-dimethoxy-4,4'-biphenylene diisocyanate.

Exemplary diols include serinol, 3-dimethylaminopropane-1,2-diol, 2-amino-2-methyl-1,3-propanediol, 2-amino-1,1-propanediol, 2-aminobutane-1,4-diol, 2-amino-1,2-propanediol, 2-amino-1,6-hexanediol, 2,5-diamino-1,6-hexanediol, 2-amino-1,7-heptanediol, 2-amino-1,5-pentanediol, 2-amino-2-ethyl-1,3-propanediol, 2,3-diamino-1,4-butanediol, 2,4-diamino-1,5-pentanediol, 2-amino-1,3-octanediol, 4-amino-3,5-heptanediol, 4-amino-1,3-hexanediol, 2-amino-2-isopropyl-1,3-propanediol, 4-amino-1,3-heptanediol, 2-amino-1,2,4-trideoxypentitol, 2,4-diamino-1,6-hexanediol.

Exemplary triol compounds include any triols including three hydroxyl groups and one amine group, such as triethanolamine.

The diols and/or triols used to synthesize the quaternized polyurethane polymers described herein may include an amine group, which may initially be protected by a protecting group, such as a BOC (tert-butyloxycarbonyl) group.

Exemplary quaternized polyurethanes are presented below. In the exemplary formulas, l may range from about 25 to 140, n may range from about 6 to 22, and m is 2 or 3.

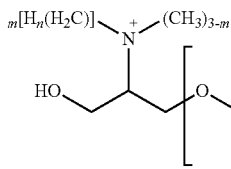
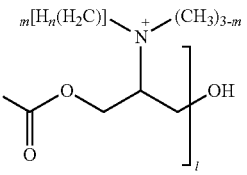

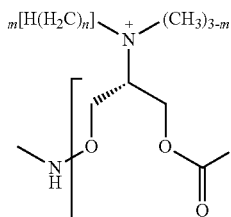
N-Alkyl-N-methyl-poly(serinol diphenylmethylene urethane)

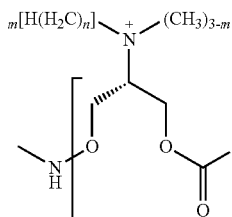
N-Alkyl-N-methyl-poly(serinol trimethylphenylene urethane)

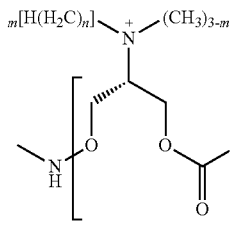
N-Alkyl-N-methyl-poly(serinol hexamethylene urethane)

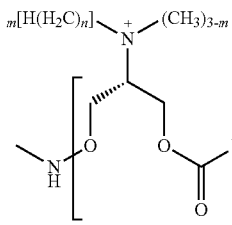
N-Alkyl-N-methyl-poly(serinol isoperone urethane)

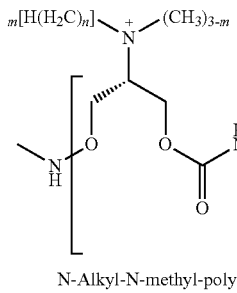
N-Alkyl-N-methyl-poly(serinol phenylene urethane)

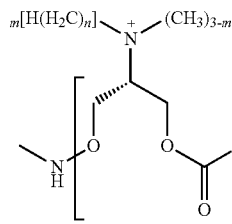
N-Alkyl-N-methyl-poly(serinol tetramethylxylylene urethane)

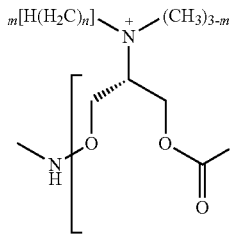
N-Alkyl-N-methyl-poly(serinol tolylene urethane)

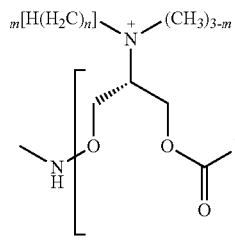
N-Alkyl-N-methyl-poly(serinol dimethoxybiphenylene urethane)

By way of example, when the polyurethane backbone is

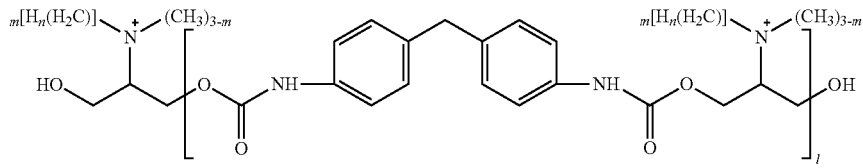

and m=3 and n=12, the composition is:

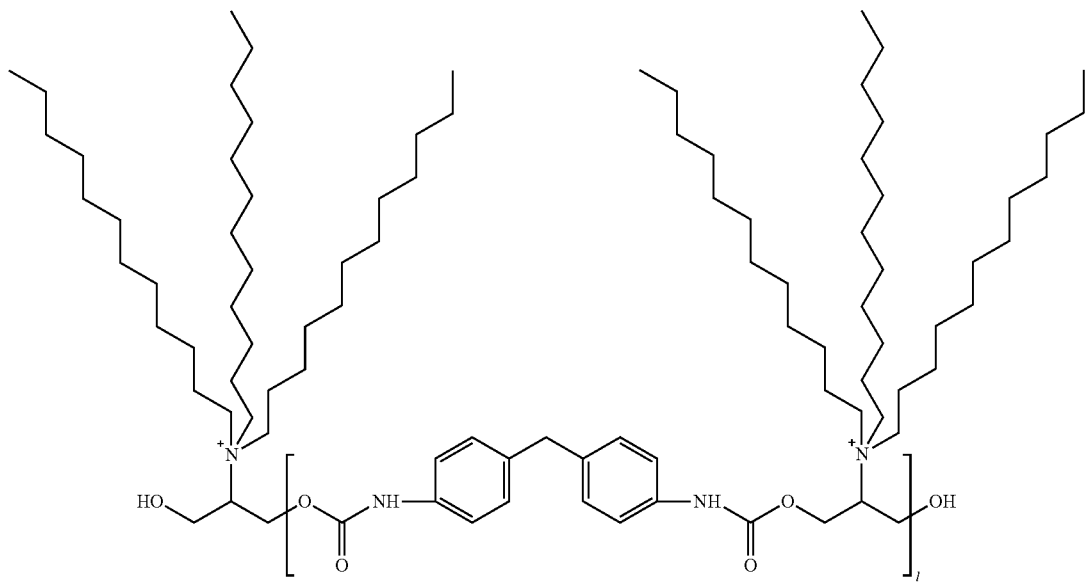

In accordance with various embodiments of the disclosure, quaternized polyurethane material may be formed as nanoparticles and/or nanofibers. Regardless of the configuration, the polyurethane material may be in solution (e.g., an organic solution) or nanosuspension (e.g., an aqueous suspension) to facilitate application of the material onto a surface, such as a medical device, filter, or other surfaces. Suitable organic solvents for use with the quaternized polyurethane material include tetrahydrofuran, methanol, chloroform, butanol, and dimethylformamide. However, the solvents are not limited to these exemplary compounds.

When applied as a nanosuspension, the quaternized polyurethane nanosuspension in an aqueous solution may be sprayed onto surfaces and dried to form nanoparticle coating. The nanoparticle coating may further be heated (e.g., to about 100° C. or to about 150° C.) to melt the material to form more stable coating on a surface. When in the form of a fiber, the quaternized polyurethane material may be spun or woven into an antimicrobial fabric.

The quaternized polyurethane compounds in accordance with various exemplary embodiments exhibit antimicrobial properties. In addition, the compounds exhibit high impact strength and abrasion resistance. These characteristics are particularly advantageous for antimicrobial applications that may use materials that desirably remain in tact for an extended period of time. Thus, the compounds described herein are advantageous over other polymer-based antimicrobial compounds that lack such characteristics.

In accordance with further embodiments of the disclosure, a method of forming a quaternized polyurethane material includes the steps of dissolving a one or more diols or triols, the diols or triols having an amine group protected with a protecting group (e.g., N-BOC-serinol), in a solvent (e.g., DMF) to form a solution, adding one or more diisocyanates (e.g., MDI) to the solution, polymerizing the solution to form polyurethane (e.g., under an nitrogen environment), precipitating the polyurethane, optionally purifying the polyurethane, removing the protecting groups, and forming the quaternized polyurethane. In accordance with various aspects of these embodiments, the polymerizing step is performed in a nitrogen environment. In accordance with further aspects, the method further includes a step of forming nanoparticles including the quaternized polyurethane. In accordance with additional aspects, the method includes the step of forming nanofibers including the quaternized polyurethane.

SPECIFIC EXAMPLES

The following non-limiting examples illustrate exemplary quaternized polyurethane materials and methods of forming the materials in accordance with various exemplary embodiments of the disclosure. These examples are merely illustrative, and it is not intended that the invention be limited to the examples.

Materials

N-BOC-serinol, 4,4'-methylene-bis(phenyl isocyanate) (4,4'-MDI), NaHCO$_3$, 1-bromohexane, 1-bromododecane, and 1-iodomethane were from Sigma-Aldrich (St. Louis, Mo.); diethyl ether from Fisher Scientific (Pittsburgh, Pa.); anhydrous chloroform, anhydrous N,N-dimethylformamide (DMF), tetrahydrofuran (THF), and trifluoroacetic acid (TFA) from EMD (Gibbstown, N.J.). Viruses were obtained from the U.S. Centers for Disease Control and Prevention (CDC) (Wuhan strain of influenza) and the American Type Tissue Collection (ATCC) (Chat strain of poliovirus). Madin-Darby canine kidney (MDCK) and HeLa cells were purchased from ATCC and maintained as previously reported (Hsu et al. 2010; Larson et al. 2010). $E.$ $coli$ and $S.$ $aureus$ bacteria were purchased from ATCC (catalog numbers 6538 and 15597, respectively) and grown in LB broth.

Equipment

The molecular weights of polymers were determined by gel permeation chromatography (GPC) using a Viscotek GPCmax VE2001 system equipped with a Viscotek I-MBMMW-3078 column and a dual detector (Viscotek 270, differential refractive index and right angle light scattering) and using DMF as a mobile phase. $^1$H-FT-NMR spectra were recorded using a Bruker Avance 600 NMR instrument. Water contact angles were measured using a VCA Optima XE instrument (AST Products) at room temperature. UV-VIS spectra were recorded using an UVmini-1240 spectrophotometer (Shimadzu Scientific Instruments). Scanning electron microscopy (SEM) images of polymer-coated surfaces subsequently sputter-coated with gold were obtained using a JEOL 6330F instrument at a 5-kV accelerating voltage. A size distribution of nanoparticles was recorded using a Nicomp 380 ZLS (Particle Sizing Systems, Santa Barbara, Calif., USA).

Synthesis of Quaternized Polyurethane

FIG. 1 illustrates an exemplary method of forming quaternized polyurethane material in accordance with exemplary embodiments of the disclosure. In the illustrated example, n=12 and m=3.

Synthesis of PU (Step 1)

N-BOC-serinol (2.6 mmol) was dissolved in 5 ml of anhydrous DMF in a 25-ml round-bottom flask and placed in a 90° C. oil bath. One mole-equivalent of 4,4'-MDI was added slowly, and polymerization was carried out for 120 h under a N2 atmosphere. Then another 2.6 mmol of N-BOC-serinol was added, and the reaction mixture was stirred for 24 h. After cooling to room temperature (RT), the reaction mixture was poured into an excess of diethyl ether to precipitate the polymer. Following removal of diethyl ether by rotary evaporation, the precipitate was dissolved in 5 ml of DMF and poured into the ether again. The purification process was carried out thrice to remove unreacted components. polyurethane was obtained after drying the precipitate at 45° C. under vacuum (98% yield, Mw of 12,200 Da).

Figure 4:
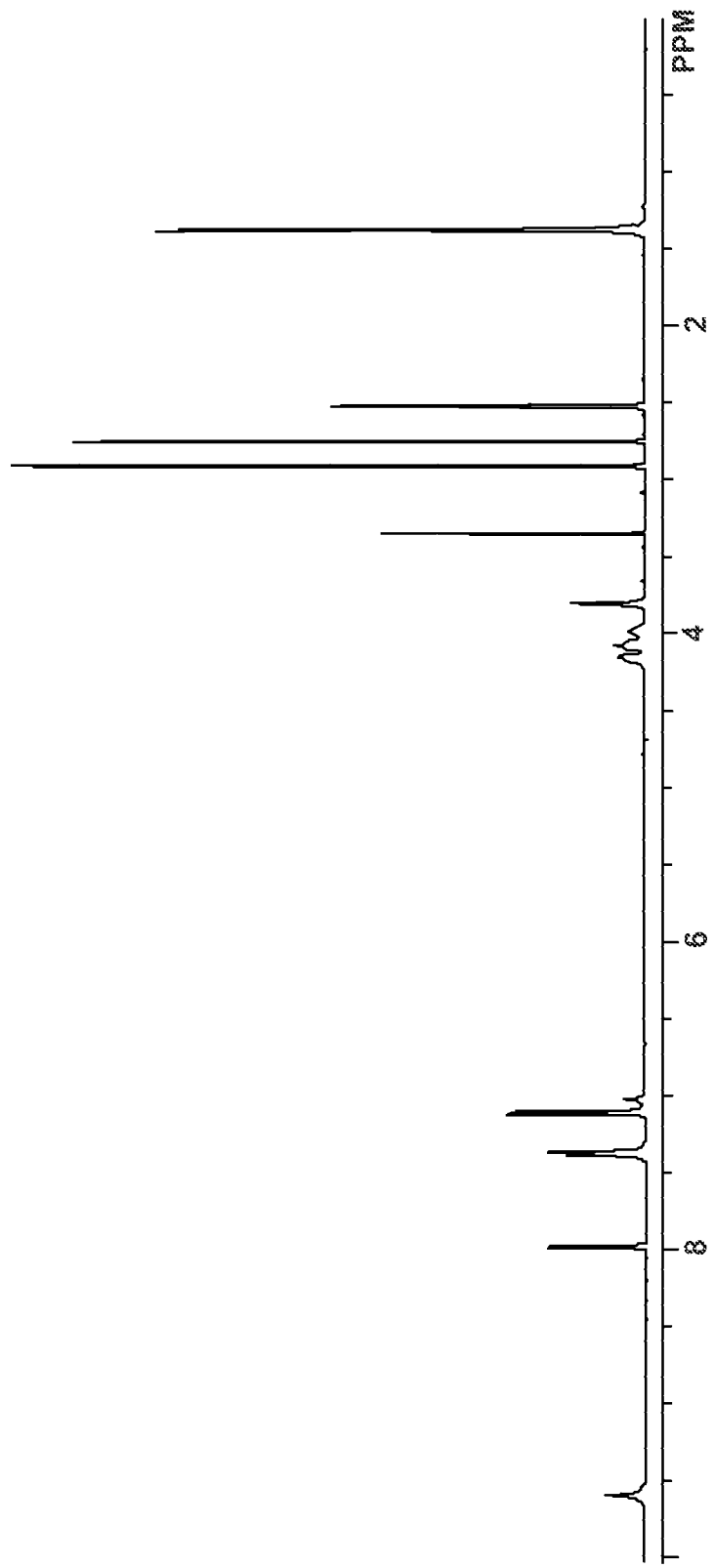
FIG. 4 illustrates $^1$H-NMR spectrum of polyurethane.

FIG. 4 illustrates $^1$H-NMR (DMSO, δ in ppm,) of polyurethane after step 1. The methyl protons in BOC groups were confirmed at 1.41 ppm. The methylene protons adjacent to oxygen in N-BOC-serinol were observed at 3.97-4.28 ppm. The aromatic protons were confirmed at 7.2 ppm. The signal at 7.48 ppm was assigned to a proton in a urethane bond.

Deprotection (Step 2)

To remove BOC protecting groups and introduce quaternizable amino groups, 1 g of PU was dissolved in 100 ml of chloroform in a 500-ml round-bottom flask. Then, 100 ml of TFA was added, and BOC deprotection was performed for 1 h at RT. After removing TFA and chloroform by rotary evaporation, the resultant polymer was dissolved in 10 ml of DMF and poured into excess of diethyl ether. The deprotected PU ($H_2$N-PU) was obtained after drying the purified precipitate for 48 h at 45° C. under vacuum (97% yield, Mw of 9,128 Da).

Figure 5:
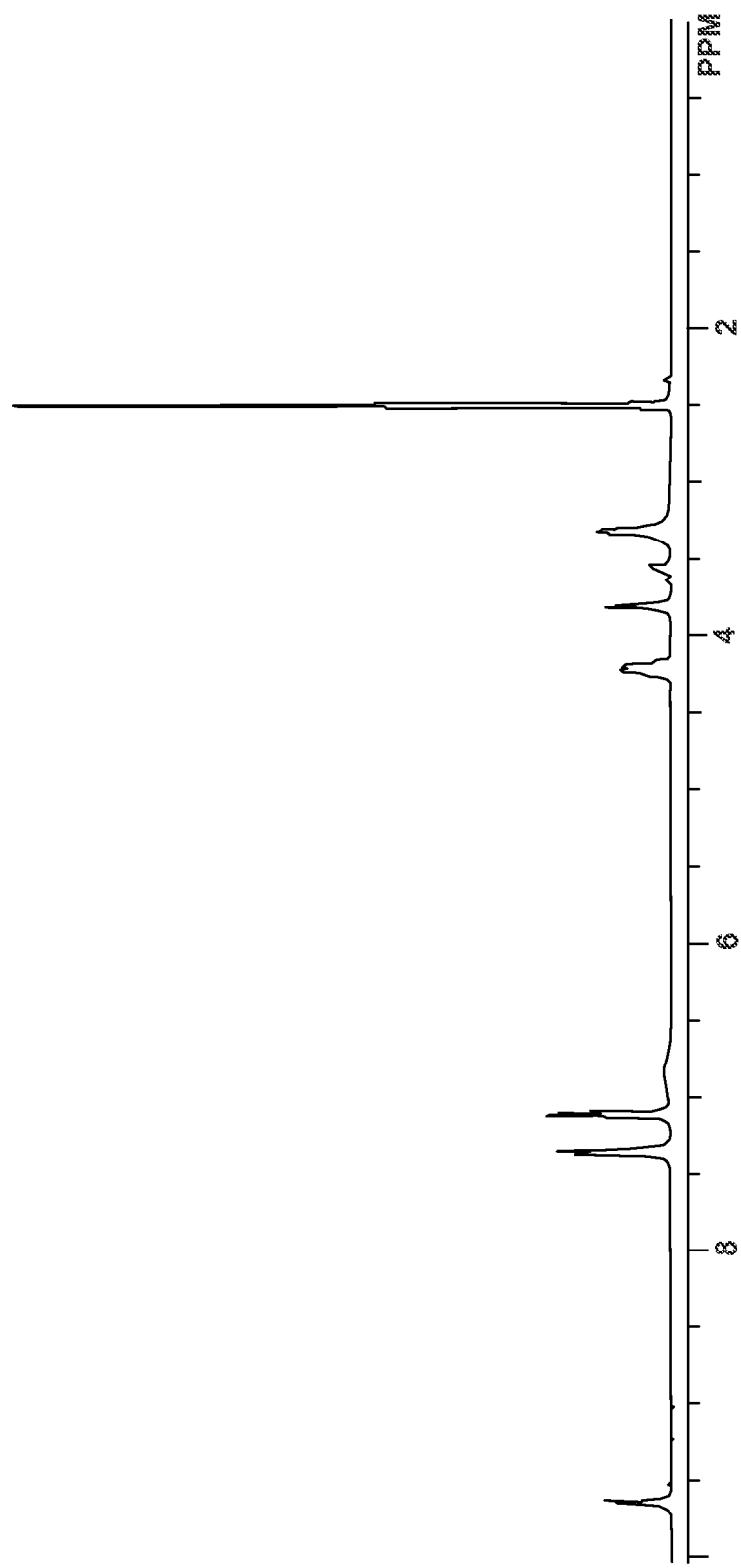
FIG. 5 illustrates $^1$H-NMR spectrum of $H_2N$-polyurethane.

FIG. 5 illustrates $^1$H-NMR (DMSO, δ in ppm) of $H_2$N-polyurethane. The signal at 1.41 ppm disappeared, indicating a complete deprotection of [$CH_2CH(NH_2)CH_2$], 7.18 (aromatic), 7.4 (OCONH). The Mw of the deprotected polyurethane was not appreciably different from the theoretical Mw, indicating the deprotection step has no adverse effect on the urethane linkages.

Quaternization of PU (Step 3)

Figure 6:
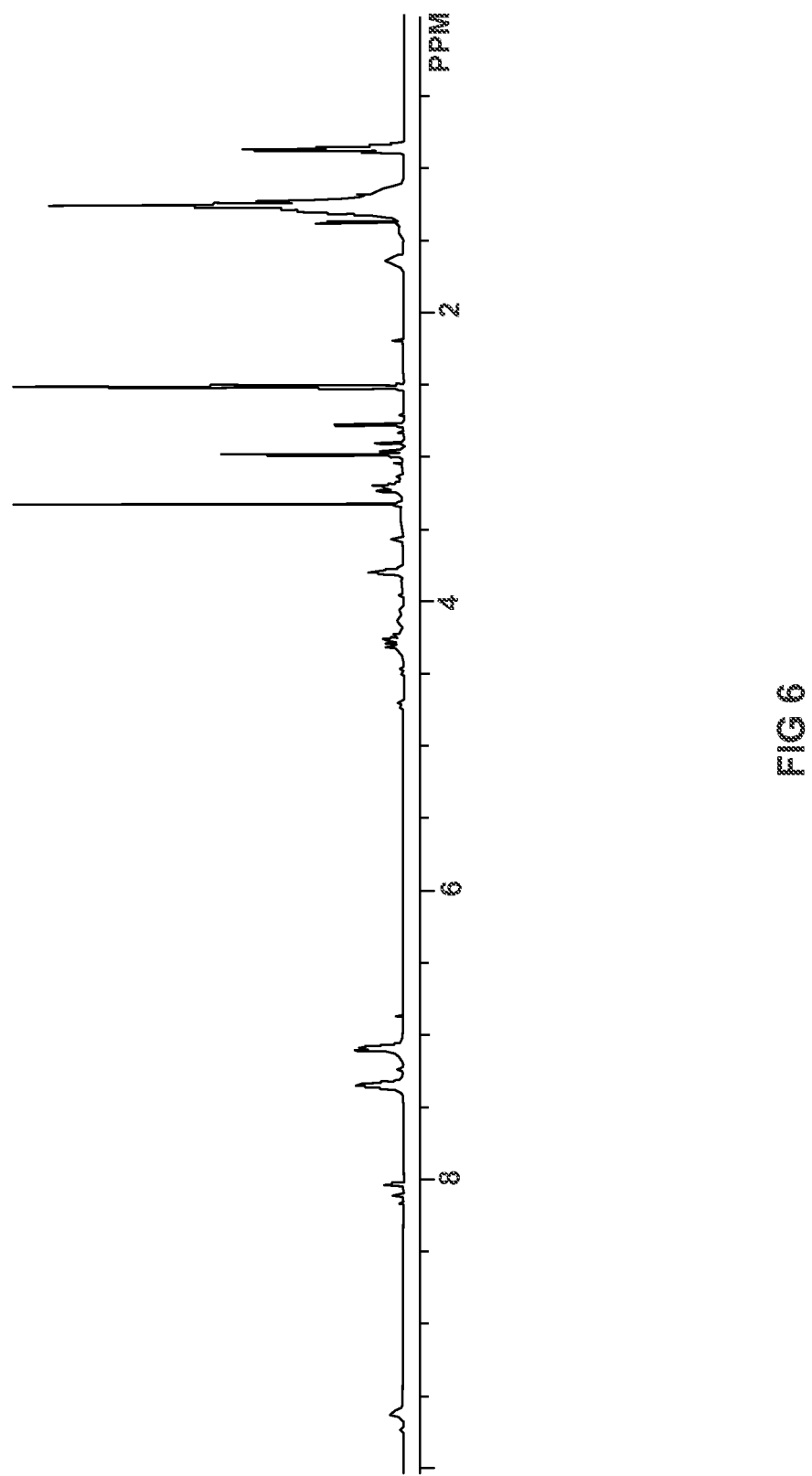
FIG. 6 illustrates $^1$H-NMR spectrum of quaternized polyurethane in accordance with exemplary embodiments of the disclosure.

$H_2$N-PU (1 g) was dissolved in 50 ml of anhydrous DMF in a 100-ml round-bottom flask, and 5 mole-equivalents of either 1-bromohexane or 1-bromododecane was added slowly, followed by 3 mole-equivalents of NaHCO$_3$. The alkylation was performed for 120 h at 95° C. under a N$_2$ atmosphere. Complete quaternization was carried out by subsequently adding 3 mole-equivalents of iodomethane for 24 h at 60° C. After removing solids by filtration, the reaction mixture was poured into excess of diethyl ether. The precipitate was recovered, dissolved in 20 ml of DMF, and re-precipitated in the ether. This process was repeated thrice to remove excess reagents. Quaternized PU derivatives were obtained after drying the precipitates for 48 h at 45° C. under reduced pressure. The quaternized polyurethanes can be designated as Quat-n-PU, where n is 6 or 12 in these illustrated examples (95% and 92% yields were obtained for Quat-6-PU and Quat-12-PU, respectively). FIG. 6 illustrates $^1$H NMR spectrum of Quat-12-PU. After quaternization, a significant change was observed between 0.5 and 2 ppm. The methyl protons and methylene protons from 1-bromododecane were confirmed at 0.9 ppm and 1.3-1.7 ppm, respectively, indicating successful alkylation with 1-bromododecane.

Preliminary Antibacterial Tests of Quat-n-PU

The preliminary antibacterial tests were carried out in 24-well cell culture plates coated with 100 µl of a 5 mg/ml Quat-n-PU solution in methanol. Bacterial suspensions (1×10$^4$ cells/200 µl) in LB broth were added in each well and incubated for 12 h at 37° C. The antibacterial activity was determined by measuring optical density of a bacterial suspension at 610 nm (Xie, Y. J., Liu, X. F., & Chen, Q. (2007). Carbohydrate Polymers, 69, 142-147.) using a microplate reader (SYNERGY Mx, BioTek). The percent increase in the optical density was calculated by comparing optical densities of bacterial suspensions before and after the incubation. After the first optical density was measured, the suspensions were removed, and the wells were washed thoroughly with distilled water. Subsequent antibacterial tests were repeated using the same procedure. Uncoated 24-well cell culture plates were used as a control.

Sample Preparation

Solution Coating

For antiviral tests, 50 mg of Quat-12-PU was dissolved in 10 ml of THF, and the solution was sprayed onto the upward-facing side of each of 30 polyethylene slides (25×25 mm) at a flow rate of 10 ml/min. For antibacterial tests, the same solution was sprayed onto the upward-facing side of each of 10 microscope glass slides (25×75 mm) at the same flow rate. Eight layers of Quat-12-PU solution were sequentially deposited, with drying between the coatings. Following drying for 48 h at 45° C., the coated slides were stored in a desiccator prior to use.

Coating with Nanoparticles

Nanoparticles were prepared by dissolving 10 mg of Quat-12-PU in 5 ml of THF. The solution was slowly added to 50 ml of deionized water in an ultrasonic bath (40 kHz, Branson 1510). After removing the THF by rotary evaporation, the nanoparticles were recovered by a centrifugation at 10,000 rpm for 10 min, followed by dispersing them in 10 ml of deionized water with gentle shaking on an orbital shaker for 72 h. After subsequent centrifugation, the Quat-12-PU nanoparticles with mean diameter of 218 nm (FIG. 9) were obtained by lyophilization.

For antiviral test-slide preparation, 10 mg of nanoparticles was dispersed in 10 ml of deionized water and sprayed onto the upward-facing side of each of 15 polyethylene slides (25×25 mm) at a flow rate of 10 ml/min. For antibacterial test-slide preparation, 10 mg of nanoparticles suspended in 10 ml of deionized water was sprayed onto the upward-facing side of five microscope glass slides (10×25 mm) at the same flow rate. Nine layers were sequentially deposited; in both cases, a deposited layer was completely dried before applying the next one.

Nanofiber Preparation

Quat-12-PU nanofibers were prepared with an electrospinning device (Subbiah et al. Subbiah, T., Bhat, G. S., Tock, R. W., Pararneswaran, S., & Ramkumar, S. S. (2005). Journal of Applied Polymer Science, 96, 557-569) consisting of a syringe with an 18-gauge needle, an aluminum collecting board, and a high-voltage supply. For electrospinning, a 20 wt % of Quat-12-PU solution in THF was electrospun at a voltage of 18 kV with a tip-to-collector distance of 15 cm. The flow rate of syringe pump connected to the syringe was set to 100 µl/min. The resultant nanofibers were carefully transferred onto the surface of a glass slide (10×25 mm).

Quantitation of Surface Quaternary Amines

The surface density of quaternary ammonium ions was measured using a fluorescein staining test (Murata, H., Koepsel, R. R., Matyjaszewski, K., & Russell, A. J. (2007). Biomaterials, 28, 4870-4879.) Samples (1 cm$^2$) coated with Quat-12-PU using either solution or nanoparticulate formulations were dipped into 10 ml of a 1% fluorescein Na solution in distilled water for 10 min at 37° C. with gentle shaking. After rinsing thrice with distilled water to remove the unbound dye, the samples were placed in 3 ml of 0.1% cetyltrimethylammonium chloride solution in which the bound dye was extracted for 20 min at 37° C. with gentle shaking. After adding 10% v/v of 100 mM of Na phosphate buffer solution (pH 8.0), the absorbance of the aqueous solution at 501 nm was recorded using a spectrophotometer, and the concentration of previously bound fluorescein was determined using the extinction coefficient of 77 mM$^{-1}$cm$^{-1}$. The quaternary ammonium group surface density was calculated assuming that one fluorescein molecule binds to each quaternary ammonium ion on the surface.

Antiviral Tests

Polyethylene slides (25×25 mm) coated with either a solution or a nanosuspension of Quat-12-PU were used to determine antiviral activity against the enveloped influenza virus (Wuhan strain, A/Wuhan/359/95) and the non-enveloped poliovirus (Chat strain). The slides were placed coated-side up into a polystyrene Petri dish, and 10 µl of either a (3.8±1.0)×105 pfu/ml poliovirus solution in Eagle's minimum essential media (EMEM) or a (5.9±1.7)×104 pfu/ml solution of influenza virus in phosphate buffered saline (PBS) was placed in the center of each slide. The virus-containing droplet was sandwiched with a plain polyethylene slide, and an eight-ounce weight was placed on the sandwiched slides to spread out the droplet. The same was done for plain control slides (control 2). Viruses were incubated between the slides for 15 min, after which time the slides were separated with tweezers and washed thoroughly with 990 µl of EMEM or PBS for poliovirus and influenza virus, respectively. The washings were collected and assayed for infectious viral particles via a plaque assay as previously described (Haldar et al. 2006; Haldar, J., An, D. Q., de Cienfuegos, L. A., Chen, J. Z., & Klibanov, A. M. (2006). Proceedings of the National Academy of Sciences of the United States of America, 103, 17667-17671; Larson, A. M., Hsu, B. B., Rautaray, D., Haldar, J., Chen, J. Z., & Klibanov, A. M. (2010). Biotechnology and Bioengineering, 108, 720-723.) Plaques were counted and compared to those in a control experiment with the viruses never sandwiched between slides (control 1) to determine antiviral activity of the coated slides.

Antiviral Assay of N,N-dodecyl,methyl-PEI Coated Slides and Poliovirus Washed with Detergent Solutions N,N-Dodecyl,methyl-PEI was synthesized as described previously (Haldar et al. 2006), and polyethylene slides (25×25 mm) coated with this polycation were tested for antiviral activities as outlined above for poliovirus, except that in the washing step the viruses were washed off the slide with 990 µl of 0.1% cetyltrimethylammonium chloride in PBS or 0.05% Tween 80 in 0.5 M NaCl solution. In controls, solutions of viruses were incubated between two plain polyethylene slides and washed with detergent solutions.

Antibacterial Tests

The plain and coated slides (five samples of each slide) were incubated with 2 ml of a bacterial suspension (10$^8$ cells) in a conical tube (Falcon) for 1 h at 37° C. and 300 rpm. One hundred µl was withdrawn from each tube, serial dilutions of the sample were plated onto LB-agar plates, and the number of colonies was counted after incubation overnight at 37° C. The antibacterial activity was expressed as log-reduction: the difference between the logarithms of viable cells incubated with plain and coated slides.

Results

Figure 7:
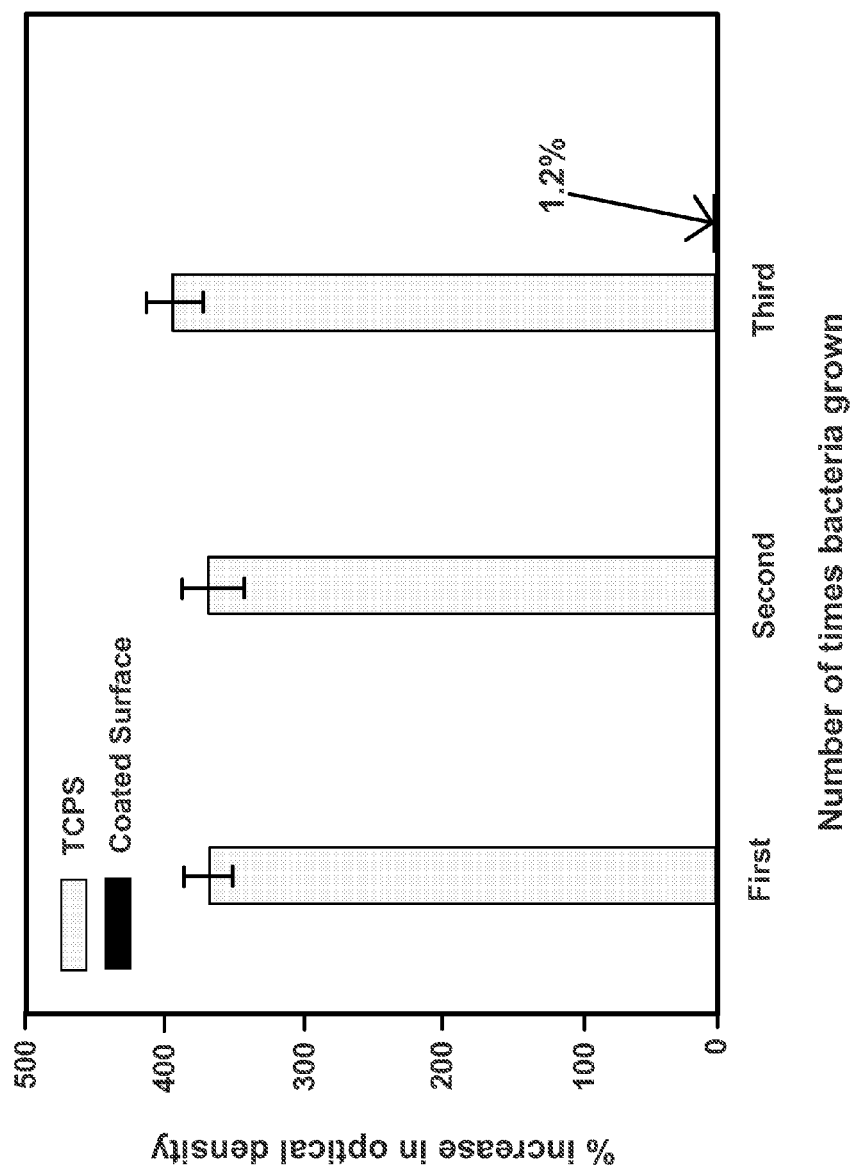
FIG. 7 illustrates antibacterial activity against *E. coli* of quaternized polyurethane in accordance with exemplary embodiments of the disclosure.
Figure 8:
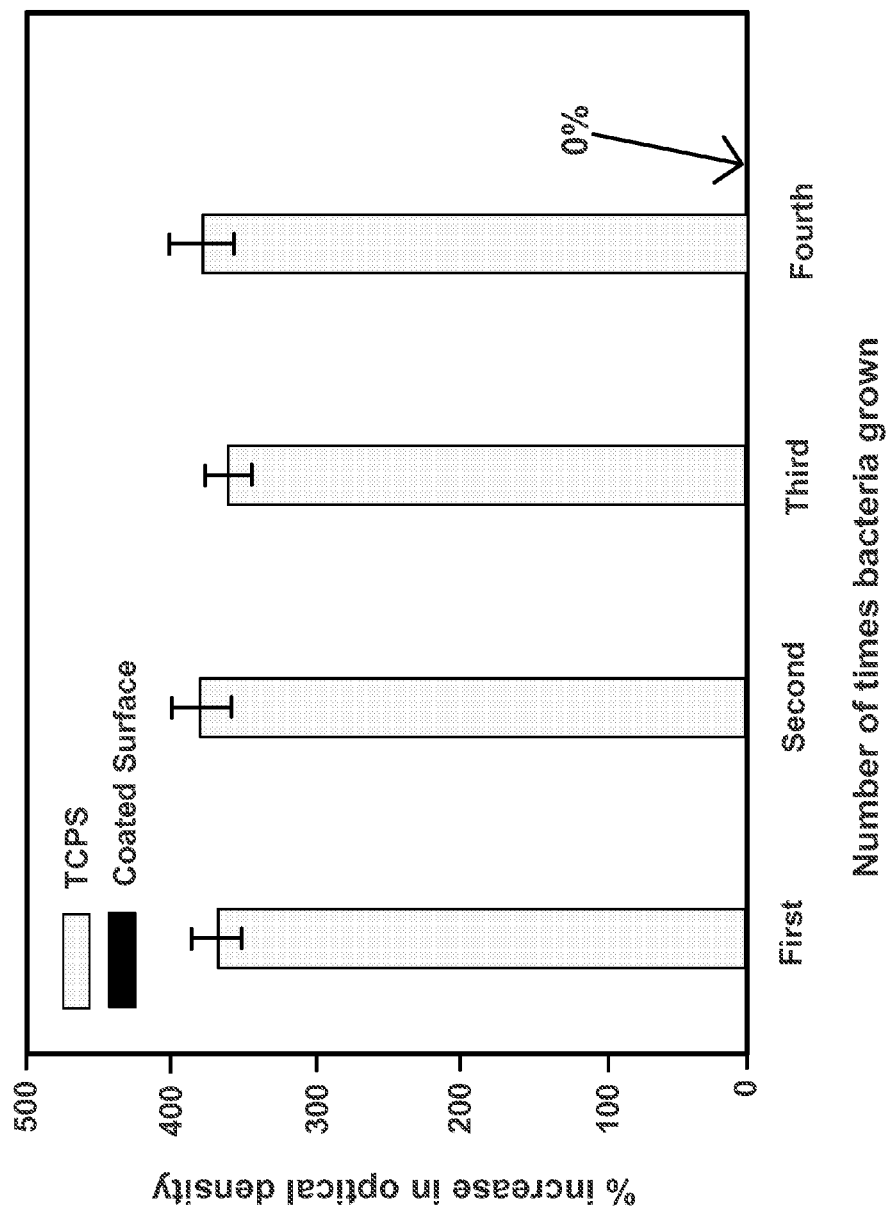
FIG. 8 illustrates antibacterial activity of quaternized polyurethane against *E. coli* In accordance with further exemplary embodiments of the disclosure.

The hydrophobic moieties in the PU system were introduced by means of alkylation by either 1-bromohexane or 1-bromododecane, followed by finishing quaternization with iodomethane, to result in Quat-6-PU and Quat-12-PU, respectively (FIG. 1). The optical density of *E. coli* suspensions LB broth incubated in 24-well culture plates coated with both polycations remained unchanged after a 12-h incubation indicating an arrest in cell growth, while a 3-fold jump in optical density was observed in the suspensions incubated in uncoated plates under the same conditions. These observations indicate that Quat-6-PU and Quat-12-PU coatings are antibacterial (FIGS. 7 and 8). The same test was conducted after exhaustively washing the coated surfaces with water to test their robustness, and no change in the optical density was observed for either the Quat-6-PU-coated or Quat-12-PU-coated plates after repeated thorough washes. Note, however, because of its greater hydrophobicity, Quat-12-PU would be expected to be more resistant to leaching, which was indeed the case (see below).

To examine the leaching of Quat-n-PU from the coated surface after wetting, we measured the changes in dynamic contact angles of polyethylene surfaces coated with Quat-6-PU and Quat-12-PU (Table I). The advancing (θA) and receding (θR) contact angles of uncoated polyethylene slide were 109° and 84°, respectively, and they did not change after a 72-h wetting at room temperature (not illustrated). The initial advancing and receding contact angles for a Quat-6-PU coated surface were 92° and 43°, respectively. After the surface was incubated in a water bath for 72 h at room temperature, the contact angles dropped to 56° for θA and 18° for θR corresponding to a 39% and 58% decrease, respectively (Table I). The initial contact angles of Quat-12-PU-coated surfaces were 106° (θA) and 71° (θR), i.e., expectedly higher (reflecting a greater hydrophobicity) than those for Quat-6-PU. A decrease in contact angles after the aqueous incubation was several fold smaller for Quat-12-PU than for Quat-6-PU coatings: only 15% ($\theta A$) and 14% ($\theta R$). These data suggest that the more hydrophobic coating is more resistant to leaching. Moreover, the Quat-12-PU coatings maintained its complete antibacterial activity even after four cycles of washing (FIG. 8).

TABLE I

Dynamic contact angles of polyethylene surfaces coated with Quat-6-PU and Quat-12-PU before and after incubation (wetting) in water.

| Polycation | Before wetting | | After wetting | |
|---|---|---|---|---|
| | $\theta_A$ | $\theta_R$ | $\theta_A$ | $\theta_R$ |
| Quat-6-PU | 92° ± 3° | 43° ± 2° | 56° ± 4° | 18° ± 3° |
| Quat-12-PU | 106° ± 5° | 71° ± 3° | 89° ± 2° | 61° ± 4° |

$\theta_A$ and $\theta_R$ are advancing and receding contact angles, respectively.

Figure 2:
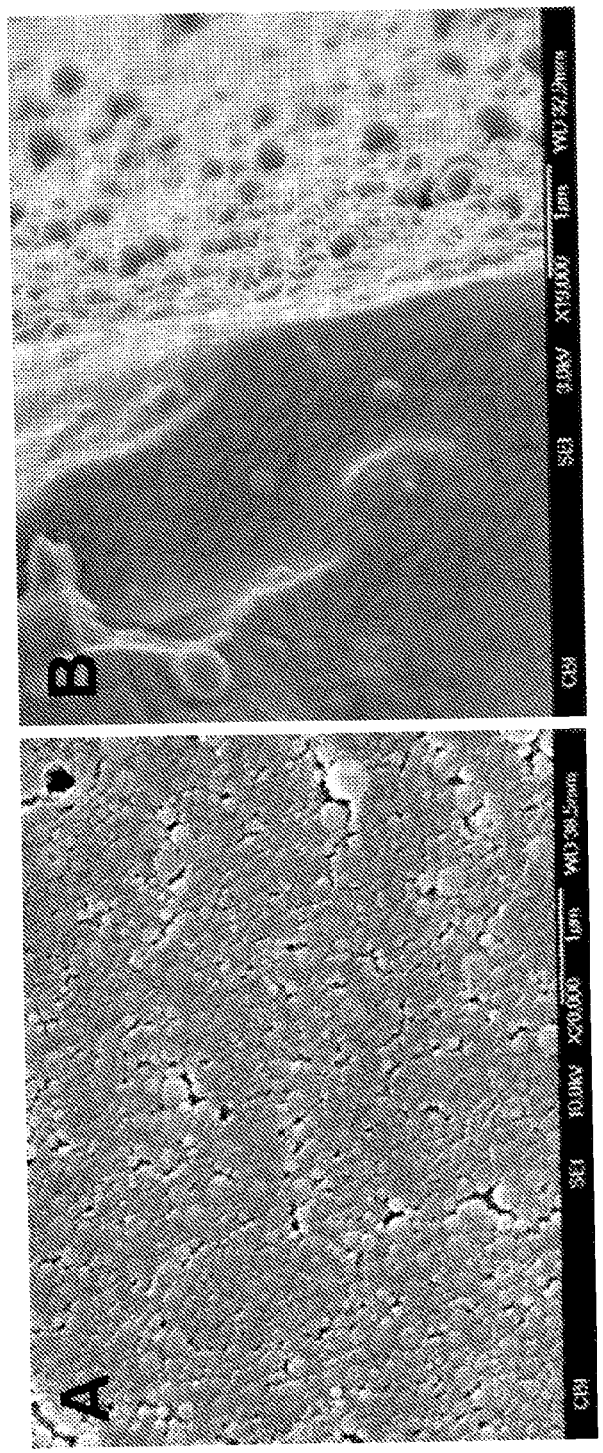
FIG. 2 illustrates SEM images of a polyethylene surface coated with quaternized polyurethane nanoparticles in accordance with exemplary embodiments of the disclosure.
Figure 9:
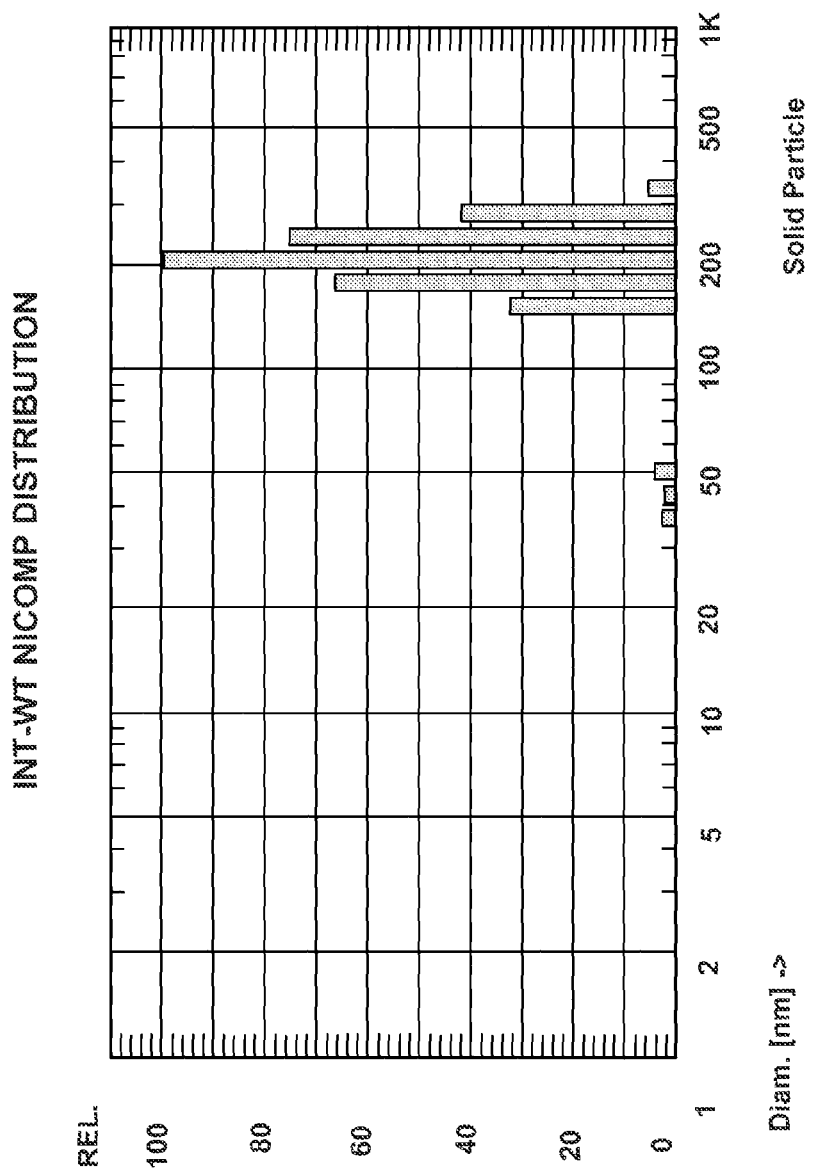
FIG. 9 illustrates size distribution of quaternized polyurethane nanoparticles evaluated by DLS in accordance with yet additional exemplary embodiments of the disclosure.

Antibacterial activity for polyQACs may depend on the surface charge density of quaternary ammonium ions. It is thought that applying additional layers of Quat-12-PU onto surfaces could increase the charge density. That was found to be indeed the case for polyethylene surfaces coated with either THF solutions or aqueous nanosuspensions of Quat-12-PU (Table II). The size of Quat-12-PU nanoparticles used for nanosuspension coating was about 218 nm (FIG. 9). As illustrated in table II, the saturation occurred after 8 coating cycles for a solution and 9 cycles for a nanosuspension, with only negligible changes in the quaternary ammonium group density on the surface thereafter. FIG. 2 illustrates SEM images of the surface coated with Quat-12-PU nanoparticles.

TABLE II

The dependence of the surface charge density of quaternary ammonium ions on the number of coating cycles of Quat-12-PU from its THF solution and an aqueous nanosuspension.

| Number of coating cycles | Charge density per cm$^2$ (×10$^{15}$) | |
|---|---|---|
| | Solution | Nanosuspension |
| 5 | 4.30 | 4.91 |
| 6 | 5.85 | 6.36 |
| 7 | 6.11 | 7.51 |
| 8 | 6.28 | 7.58 |
| 9 | 6.27 | 7.61 |
| 10 | 6.28 | 7.61 |
| 11 | n.d. | 7.60 |

As illustrated in Table III(a), glass surfaces coated with either a THF solution or an aqueous nanosuspension of Quat-12-PU showed excellent antibacterial activities against airborne E. coli and S. aureus: no colonies were observed on the surfaces coated with either formulation, whereas many colonies were visible on plain glass surfaces.

TABLE III(a)

The number of bacterial colonies observed on 1 cm$^2$ of uncoated and Quat-12-PU-coated (using either a THF solution or an aqueous nanosuspension) glass surfaces.

| | | Slide coated with | | | |
|---|---|---|---|---|---|
| Plain slide | | THF solution | | Aqueous nanosuspension | |
| S. aureus | E. coli | S. aureus | E. coli | S. aureus | E. coli |
| 127 ± 13 | 121 ± 11 | 0 | 0 | 0 | 0 |

As illustrated in Table III(b), glass surfaces coated with either a THF solution or an aqueous nano-suspension of Quat-12-PU showed excellent antibacterial activities against waterborne E. coli and S. aureus. The log-reduction of S. aureus and E. coli incubated with slides coated with the THF solution was 7.1 and 6.92, respectively. Interestingly the log-reduction of both bacteria incubated with slides prepared by the aqueous nanosuspension was higher than that of the THF solution coated slides: 7.78 and 7.76 for S. aureus and E. coli, respectively. The higher log-reduction might be caused by the higher surface charge density of quaternary ammonium ions on the slides coated with the aqueous nanosuspension as listed in Table 2.

TABLE IIII(b)

The log-reduction of cells inoculated with Quat-12-PU-coated (using either a THF solution or an aqueous nanosuspension) glass surfaces

| Slide coated with | | | |
|---|---|---|---|
| THF solution | | Aqueous nanosuspension | |
| S. aureus | E. coli | S. aureus | E. coli |
| 7.1 ± 0.04 | 6.92 ± 0.03 | 7.78 ± 0.05 | 7.76 ± 0.03 |

To examine the antiviral activities of Quat-12-PU, polyethylene slides coated with its THF solution or aqueous nanosuspensions were incubated with two distinct types of pathogenic viruses: influenza (enveloped) and poliovirus (non-enveloped). As seen in Table IV, regardless of the mode of coating, the resultant surfaces were completely lethal to the human Wuhan strain of influenza virus. Presumably, the hydrophobic Quat-12-PU coatings disrupt the lipid envelope of the virus protecting its RNA, as was previously demonstrated for N,N-dodecyl,methyl-PEI coatings (Hsu, B. B., Wong, S. Y., Hammond, P. T., Chen, J. Z., & Klibanov, A. M. (2010). Proceedings of the National Academy of Sciences of the United States of America, 108, 61-66). However, Quat-12-PU-coated surfaces failed to inactivate poliovirus (Table IV).

TABLE IV

Antiviral activities of uncoated and Quat-12-PU-coated (using either a THF solution or an aqueous nanosuspension) polyethylene slides.

| Virus | No slide | Uncoated slide | Slide coated with a solution | Slide coated with a nanosuspension |
|---|---|---|---|---|
| influenza (pfu/ml) | (5.9 ± 1.7) × 10$^4$ | (2.2 ± 0.3) × 10$^4$ | 0 | 0 |
| poliovirus (pfu/ml) | (3.8 ± 1.0) × 10$^5$ | (1.7 ± 0.4) × 10$^5$ | (1.6 ± 0.4) × 10$^5$ | (1.4 ± 0.5) × 10$^5$ |

Figure 3:
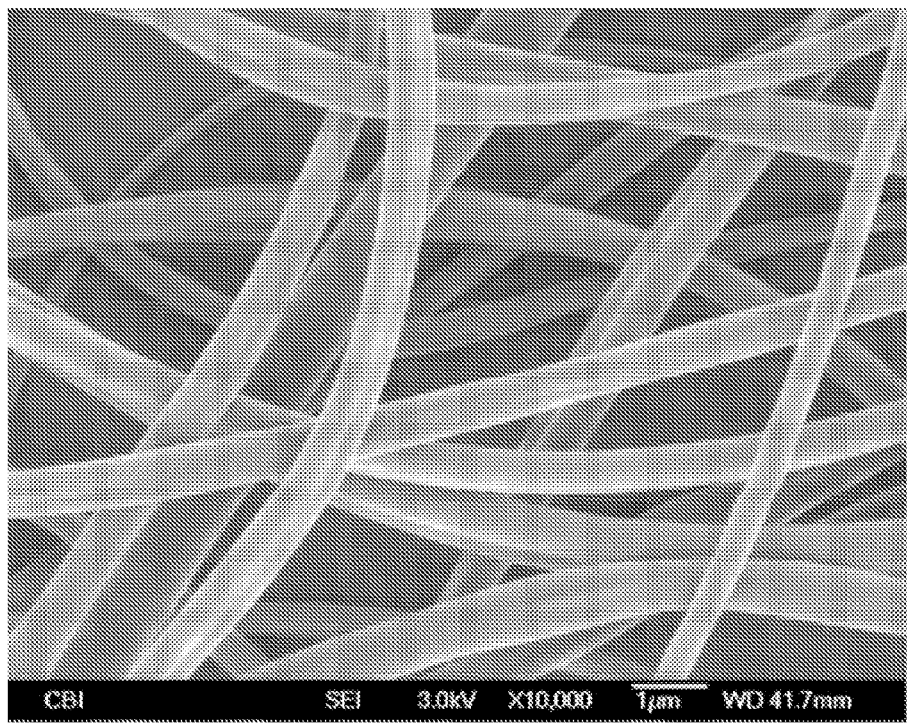
FIG. 3 illustrates an SEM image of quaternized polyurethane nanofibers in accordance with exemplary embodiments of the disclosure.

To expand the utility of Quat-12-PU beyond surface coatings, we processed the polycationic polymer into nanofibers using an electrospinning method. Specifically, solutions of Quat-12-PU in THF were electrospun to obtain continuous and uniform nanofibers seen in FIG. 3. These nanofibers were found to exhibit excellent antibacterial activities against both E. coli and S. aureus (Table V). Like with Quat-12-PU-coated surfaces tested, no bacterial colonies were observed on the nanofiber surfaces. With polymeric nanofibers having potential to be used in fabrics, filters, and medical devices, those made from Quat-12-PU would have an added benefit of being antimicrobial.

TABLE V

The number of bacterial colonies observed on surfaces of a plain glass slide (used as a control) and slides to which airborne bacteria were applied on top of a Quat-12-PU nanofiber coating.

| Uncoated glass slide | | Quat-12-PU nanofibers | |
|---|---|---|---|
| S. aureus | E. coli | S. aureus | E. coli |
| 133 ± 12 | 121 ± 10 | 0 | 0 |

FIG. 7 illustrates antibacterial activity of Quat-6-PU-coated 24-well plates against *E. coli*. No changes of optical density were observed with coated surfaces until a second washing. A significant increase in the optical density was observed with uncoated surfaces in every test. TCPS in the figures refers to tissue culture polystyrene.

FIG. 8 illustrates antibacterial activity of Quat-12-PU against *E. coli*. No changes of optical density were observed with coated surfaces after any washing cycle while a significant increase in the optical density was observed with uncoated surfaces.

Measurement of the Size of Quat-12-PU Nanoparticles Using Dynamic Light Scattering (DLS)

Nanoparticles were dispersed in deionized water in a borosilicate glass cuvette, and the size distribution was recorded by a Nicomp 380 ZLS (Particle Sizing Systems, Santa Barbara, Calif.). FIG. 9 illustrates that two populations of sizes were observed with mean diameters of 47 nm and 218 nm; the vast majority of the nanoparticles were in the latter group.

New antimicrobial polyQAC, Quat-12-PU, which can be readily processed into solutions, nanosuspensions, and nanofibers have been prepared. However created, Quat-12-PU surfaces efficiently (with at least a 100-fold reduction in microbial titers) inactivated both *S. aureus* and *E. coli* bacteria, as well as influenza viruses.

In accordance with additional examples, N-BOC-serinol (0.986 g, 5 mmol) was placed in a 25 ml round bottom flask and melted at 90° C. under a nitrogen atmosphere. Hexamethylene diisocyanate (HDI, 0.843 g, 5 mmol) was added slowly and the polymerization was performed for 7 days to form the urethane bonds. After cooling down to ambient temperature, the mixture was dissolved in 2 ml anhydrous chloroform and poured into excess anhydrous diethyl ether to precipitate out the polymer. The purification process was carried out twice and the precipitates were washed in 100 ml of anhydrous diethyl ether overnight to remove unreacted HDI. Polyurethane (PU) was obtained after drying at 45° C. under vacuum (yield: 97%).

As synthesized PU (1.5 g) was dissolved in 50 ml dichloromethane (DCM) in a 250 ml round bottom flask. Trifluoroacetic acid (TFA, 10 ml) was added and BOC de-protection was performed for 1 h at room temperature. After removing TFA and DCM by rotary evaporation, the polymer was purified using dialysis in water at room temperature for 2 days. The dialyzed solution was freeze-dried and a pale yellowish solid (NH2-PU) was obtained (yield: 96%).

A solution of 1 g of NH$_2$-PU and 2.1 g of Na$_2$CO$_3$ in 100 mL of anhydrous dimethylformamide (DMF) and 6.18 mL of 1-bromododecane were mixed and stirred at 100° C. for 5 h. After removing the solids by filtration under reduced pressure, 0.934 mL of iodomethane was added, followed by stirring at 60° C. for 24 h in a sealed bottle. The resultant was poured into excess anhydrous diethyl ether to precipitate out the polymer and dried at room temperature under vacuum overnight. Similar antibacterial results were obtained using coatings formed using HDI-based polyurethane materials formed according to this method. The resultant polyurethane is also expected to produce similar results as above with regard to viruses, such as those noted above. In addition, the polyurethanes described herein are thought to efficiently inactivate methicillin-resistant *Staphylococcus aureus* (MRSA) bacteria.

The present invention has been described above with reference to a number of exemplary embodiments and examples. It should be appreciated that the particular embodiments shown and described herein are illustrative of the preferred embodiments of the invention and its best mode, and are not intended to limit the scope of the invention as set forth in the claims. It will be recognized that changes and modifications may be made to the embodiments described herein without departing from the scope of the present invention. These and other changes or modifications are intended to be included within the scope of the present invention, as expressed in the following claims and the legal equivalents thereof.

The invention claimed is:

1. An antimicrobial compound, wherein the compound comprises quaternized polyurethane comprising an end group comprising a quaternary compound, and wherein the quaternized polyurethane has a general structure of:

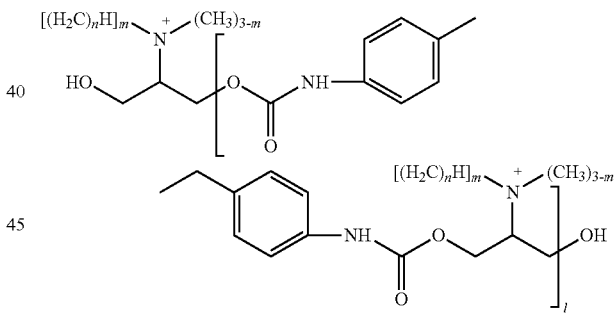

wherein l ranges from about 20 to about 200, m is 2 or 3 and n is 6-22.

2. The antimicrobial compound of claim 1, wherein the quaternized polyurethane is synthesized from one or more diisocyanates and one or more compounds selected from the group of one or more diols comprising an amine group and one or more triols comprising an amine group.

3. The antimicrobial compound of claim 2, wherein one or more diisocyanates are selected from one or more of the group consisting of isophorone diisocyanate, 1,4-phenylene diisocyanate, 1,3-phenylene diisocyanate, toluene-2,4-diisocyanate, toluene-2,6-diisocyanate, 2,4,6-trimethyl-1,3-phenylene diisocyanate, tetramethylene diisocyanate, octamethylene diisocyanate, 1,3-bis(1-isocyanato-1-methylethyl)benzene, 4,4'-methylenebis(phenyl isocyanate), 3,3'-dimethyloxy-4,4'-bisphenylene diisocyanate, 1,8 diisocyanateoctane, α,α,α',α'-tetramethyl-1,3-xylylene diisocyanate, and 3,3'-dimethoxy-4,4'-biphenylene diisocyanate.

4. The antimicrobial compound of claim 2, wherein one or more diols are selected from the group consisting of serinol, 3-dimethylaminopropane-1,2-diol, 2-amino-2-methyl-1,3-propanediol, 2-amino-1,1-propanediol, 2-aminobutane-1,4-diol, 2-amino-1,2-propanediol, 2-amino-1,6-hexanediol, 2,5-diamino-1,6-hexanediol, 2-amino-1,7-heptanediol, 2-amino-1,5-pentanediol, 2-amino-2-ethyl-1,3-propanediol, 2,3-diamino-1,4-butanediol, 2,4-diamino-1,5-pentanediol, 2-amino-1,3-octanediol, 4-amino-3,5-heptanediol, 4-amino-1,3-hexanediol, 2-amino-2-isopropyl-1,3-propanediol, 4-amino-1,3-heptanediol, 2-amino-1,2,4-trideoxypentitol, and 2,4-diamino-1,6-hexanediol.

5. The antimicrobial compound of claim 2, wherein one or more triols include an amine group.

6. The antimicrobial compound of claim 2, wherein the one or more diols comprising an amine group and one or more triols comprising an amine group are initially protected by a protecting group.

7. The antimicrobial compound of claim 1, wherein the compound comprises nanoparticles having an average diameter of about 25 nm to about 300 nm.

8. The antimicrobial compound of claim 1, wherein the compound comprises nanofibers having an average diameter of about 150 nm to about 300 nm.

9. The antimicrobial compound of claim 1, wherein the antimicrobial material compound comprises an aqueous suspension.

10. The antimicrobial compound of claim 1, wherein n ranges from about 6 to about 12.

11. The antimicrobial compound of claim 1, wherein the antimicrobial material compound comprises a solution.

12. The antimicrobial compound of claim 11, wherein the solution comprises an organic solvent.

13. The antimicrobial compound of claim 12, wherein the solvent comprises a compound selected from the group consisting of tetrahydrofuran, methanol, chloroform, butanol, and dimethylformamide.

14. A device comprising the quaternized polyurethane of claim 1.

15. The device of claim 14 comprising a filter.

16. The device of claim 14 comprising a medical device.

17. The device of claim 14 comprising a plurality of layers of quaternized polyurethane.

18. A method of forming the quaternized polyurethane of claim 1, the method comprising the steps of:
dissolving a one or more diols or triols, the diols or triols having an amine group protected with a protecting group, in a solvent to form a solution;
adding one or more diisocyanates to the solution;
polymerizing the solution to form the polyurethane;
precipitating the polyurethane;
removing protecting group; and
forming the quaternized polyurethane.

19. The method of claim 18, wherein the polymerizing step is performed in a nitrogen environment.

20. The method of any claim 18, further comprising the step of forming nanoparticles.

21. The method of any claim 18, further comprising the step of forming nanofibers.

22. The method of claim 21, further comprising the step of weaving the nanofibers.

23. An antimicrobial Quat-n-PU material, having the general formula of:

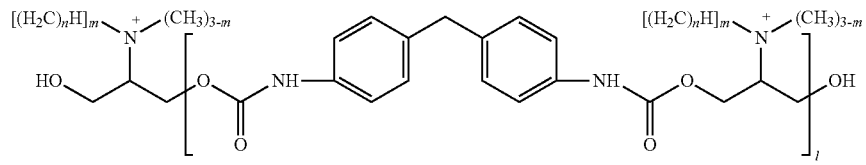

wherein I ranges from about 20 to about 200, m is 2 or 3, n is 6-22 and wherein a molecular weight of the antimicrobial Quat-n-PU material ranges from about 5,000 to about 50,000 Da.

24. The antimicrobial Quat-n-PU material of claim 23, wherein the material exhibits antiviral behavior against enveloped viruses.

25. The antimicrobial Quat-n-PU material of claim 23, wherein the material is antibacterial.

26. A device formed from the antimicrobial Quat-n-PU material of claim 23.

27. The antimicrobial compound of claim 1, wherein I ranges from about 25 to 140.

28. The antimicrobial compound of claim 23, wherein I ranges from about 25 to 140.

29. The antimicrobial compound of claim 1, wherein n is about 6.

30. The antimicrobial compound of claim 1, wherein n is about 12.

31. The antimicrobial compound of claim 23, wherein n is about 6.

32. The antimicrobial compound of claim 23, wherein n is about 12.

* * * * *